United States Patent
Messier et al.

(10) Patent No.: US 7,320,758 B2
(45) Date of Patent: Jan. 22, 2008

(54) METHOD FOR CONTROL OF MICROORGANISMS IN METALWORKING FLUID

(75) Inventors: Pierre Jean Messier, Saint Sauveur (CA); Joe Tanelli, Winooski, VT (US); Jean-Pierre St-Louis, Prevost (CA); David Ohayon, Dollard-des-Ormeaux (CA); Gerald Bruno, Jr., St George, VT (US)

(73) Assignee: Triosyn Holding, Inc., Williston, VT (US)

( * ) Notice: Subject to any disclaimer, the term of this patent is extended or adjusted under 35 U.S.C. 154(b) by 13 days.

(21) Appl. No.: 10/903,410

(22) Filed: Jul. 30, 2004

(65) Prior Publication Data

US 2005/0025739 A1  Feb. 3, 2005

Related U.S. Application Data

(60) Provisional application No. 60/491,217, filed on Jul. 30, 2003.

(51) Int. Cl.
*B01D 37/00* (2006.01)
*C02F 1/50* (2006.01)

(52) U.S. Cl. .................. 210/668; 210/753; 210/764; 210/765

(58) Field of Classification Search .............. 210/668, 210/764
See application file for complete search history.

(56) References Cited

U.S. PATENT DOCUMENTS

| | | | |
|---|---|---|---|
| 3,817,860 A | 6/1974 | Lambert et al. | |
| 3,923,665 A | 12/1975 | Lambert et al. | |
| 4,238,477 A | 12/1980 | Lambert et al. | |
| 4,420,590 A | 12/1983 | Gartner | |
| 4,482,462 A | 11/1984 | Johnson | |
| 4,719,227 A | 1/1988 | Schade et al. | |
| 4,925,582 A | 5/1990 | Bennett | |
| 4,945,109 A | 7/1990 | Rayudu | |
| 5,132,046 A | 7/1992 | Edebo et al. | |
| 5,156,665 A | 10/1992 | Sherba et al. | |
| 5,179,127 A | 1/1993 | Hsu | |
| 5,328,926 A | 7/1994 | Oppong | |
| 5,374,631 A | 12/1994 | Oppong et al. | |
| 5,512,191 A | 4/1996 | Krueger | |
| 5,589,138 A | 12/1996 | Drechsler | |
| 5,633,222 A | 5/1997 | Skold et al. | |
| 5,639,452 A | 6/1997 | Messier | |
| 6,616,835 B2 | 9/2003 | Jensen | |
| 7,147,824 B2 * | 12/2006 | Rossmoore | 422/37 |
| 2003/0098276 A1 | 5/2003 | Carlson | |

* cited by examiner

*Primary Examiner*—Peter A. Hruskoci
(74) *Attorney, Agent, or Firm*—Goodwin Procter LLP

(57) ABSTRACT

A method for disinfecting microorganisms in metalworking fluids without leaving behind unacceptable amount of chemicals in the treated fluids. The method comprises passing the fluid in a recirculating cooling system through a filter, which contains a demand disinfectant, preferably an iodinated resin. The iodinated resin inhibits the growth of microorganism in the fluid, which is then cycled back into the system. The present invention also relates to a filter and system for disinfecting microorganisms in metalworking fluids.

22 Claims, 2 Drawing Sheets

METHOD FOR CONTROL OF MICROORGANISMS IN METALWORKING FLUID

CROSS-REFERENCE TO RELATED APPLICATION

This application claims the benefit of priority to U.S. Provisional Application No. 60/491,217 filed on Jul. 30, 2003, which is incorporated herein by reference in its entirety.

BACKGROUND OF THE INVENTION

Metalworking fluids, such as lubricants and coolants, are widely used to provide more efficient metal process operations such as cutting, turning, drilling, grinding, milling, rolling and the like. Such fluids function to lubricate and cool the metal and tools used in the metalworking operations, and to facilitate removal of chips during turning, grinding, and similar operations. They can also be used to protect metals and tools against corrosion and rust formation. Metalworking fluids are important to many machine operations, because they increase production outputs, increase tool life, and enhance surface finish of the metal pieces being processed.

Metalworking fluids used to date generally fall into four categories: (1) straight oils, usually light mineral oils or kerosene; (2) soluble oils, also referred to as water-soluble emulsions, which contain oil and surfactants for emulsifying the oil; (3) semi-synthetic types, which contain relatively small amounts of oil and large percentages of surfactants or detergents and are typically provided as an oil-in-water emulsion; and (4) synthetic or chemical types, which contain no oil, but rely on various chemical compounds to achieve desired properties. The metalworking fluid formulations in the first three categories usually require surfactants for reducing surface tension.

Metalworking fluids are susceptible to the infestation and growth of microorganisms such as bacteria, fungi and yeast. Frequently, these microorganisms can cause the buildup of slime and sludge, the clogging of lines and filters, the deterioration of the properties of the metalworking fluid itself, facilitated corrosion, and health and odor problems. When affected or deteriorated by the growth of microorganisms, the metalworking fluid loses many of its essential properties. The pH of the fluid may drop and other chemical changes may occur until the fluid can no longer impart adequate lubricating, cooling or anti-corrosive properties. At this point, the fluid must be replaced with fresh metalworking fluid, which is costly.

It has been a conventional practice to add bactericides to metalworking fluids to minimize the microbial degradation of such fluids. For example, formalin or compounds giving off formalin are well-known antimicrobial agents used in metalworking fluids. However, since formalin is questionable from health and environmental aspects, there is every reason to avoid the use of formalin or compounds giving off formalin. Quaternary ammonium compounds, alkanolamine compounds and secondary amine compounds are also known antimicrobial agents. See for example U.S. Pat. Nos. 4,925,582, 5,132,046, 5,512,191 and 5,633,222.

Iodopropargyl compounds, which contain a propargyl group and iodine, are known to be useful in controlling bacteria and fungi in metalworking fluids. U.S. Pat. Nos. 4,719,227, 4,945,109 and 5,179,127 disclose various iodopropargyl compounds useful as microbicidal agents for the preservation of metalworking fluids. U.S. Pat. Nos. 5,156,665, 5,328,926 and 5,374,631 disclose synergistic combinations of iodopropargyl compounds and other compounds for the control of fungal or bacterial growth in metalworking fluids.

However, such bactericides as described above may exhibit good biocidal activities against certain microorganisms but may not be effective against other types of microorganisms, resulting in restricted applicability of the bactericides. Moreover, physical conditions, such as high temperatures, and chemical reactivity with ingredients present in the metalworking fluids often diminish or eliminate the effectiveness of the bactericides. For example, many metalworking fluids contain organic materials which may react with a specific bactericide and render the bactericide ineffective. Therefore, the bactericides may decompose or become inactive over time, so that they usually posses a fairly short useful life and need to be replenished often or even completely replaced. In addition, the use of bactericides at high concentrations imposes adverse effects on the human body, for example, it may cause skin irritation, dermatitis or other health problems. There may also be considerable environmental problems associated with disposal of used metalworking fluids, due in large part to the presence of these additives and other contaminants. Another disadvantage of adding bactericides is that additional manpower or devices are required to maintain a relatively constant concentration of the bactericide in the metalworking fluid.

Apparatuses have been developed in the art for the disinfection of metalworking fluids. U.S. Pat. No. 5,589,138 discloses an apparatus for regenerating metalworking fluids by controlled addition of a chelating agent to sequester metals dissolved in the fluids. The apparatus includes monitoring means for determining the presence of free metal ions in the fluid, testing means for determining the concentration of free metal ions if present, and addition means for adding, in a controlled manner, a chelating agent for sequestering the free metal ions.

U.S. Pat. No. 4,482,462 discloses a device for treating process fluids such as metalworking fluids within a closed chamber with a chemical reactant, preferably a triiodated quaternary amine anion exchange resin. The device includes a compartment for containing the chemical reactant and a port for allowing flow of the process fluid therethrough. The device is characterized by including recirculation means for alternately drawing at least a portion of the process fluid into the compartment through the port to bring the portion of the process fluid into direct contact with the chemical reactant to treat the fluid, e.g., dissolving and/or reacting with a portion of the chemical reactant with the portion of the process fluid. The recirculation means then forces the portion of the process fluid out of the compartment through the same port to circulate the dissolved chemical reactant, such as iodine, through the remaining process fluid within the closed chamber.

U.S. Pat. No. 6,616,835 describes a coolant recycling system comprising a support frame, a first tank for receiving contaminated coolant, a second tank for receiving a volume of water and coolant concentrate, and a third tank for treating and cleaning the contaminated coolant. The third tank is provided with an ozone applicator which applies a specific volume of ozone to the coolant during the mixing of the coolant within the third tank which kills microorganisms.

U.S. Patent Application Publication No. 20030098276 describes a filter and method for removing undesirable particulates and bacteria from metalworking fluids. The method comprises providing an enclosed channel for fluid flow and passing the fluid flow through a filter material comprising a metal alloy consisting primarily of copper and zinc and further comprising metal fiber wools.

However, the prior art apparatuses are complex in construction and operation. Moreover, these apparatuses either involve addition of chemicals into the metalworking fluids or inevitably leave behind chemicals in the treated fluids, which may impose health and environmental problems.

There remains a need for a system that is easy to operate and exhibits prolonged biocidal effects in metalworking fluids without leaving behind unacceptable amount of chemicals in the treated fluids.

SUMMARY OF THE INVENTION

It is an object of the present invention to provide a method for controlling microorganisms in metalworking fluids without leaving behind unacceptable amount of chemicals in the treated fluids.

It is another object of the present invention to provide a filter system capable of counteracting the propagation of undesirable microorganisms in metalworking fluids without leaving behind unacceptable amount of chemicals in the treated fluids.

It is a further object of the present invention to provide a filter system which exhibits prolonged biocidal activities in metalworking fluids.

It is also an object of the present invention to provide a biocidal filter system which is easy to operate for disinfecting metalworking fluids.

It is another object of the present invention to provide a method of controlling the growth of microorganisms in a metalworking fluid, comprising passing the metalworking fluid through a filter containing a demand disinfectant, the demand disinfectant being an iodinated resin.

It is yet another object of the present invention to provide a system for controlling microorganisms in a metal working fluid, the system comprising: (a) means for providing a flow path for the movement of the metalworking fluid; and (b) a filter disposed in the flow path for the metalworking fluid to flow through the filter, the filter comprising a demand disinfectant, the demand disinfectant being an iodinated resin.

DETAILED DESCRIPTION OF THE INVENTION

Figure 1:
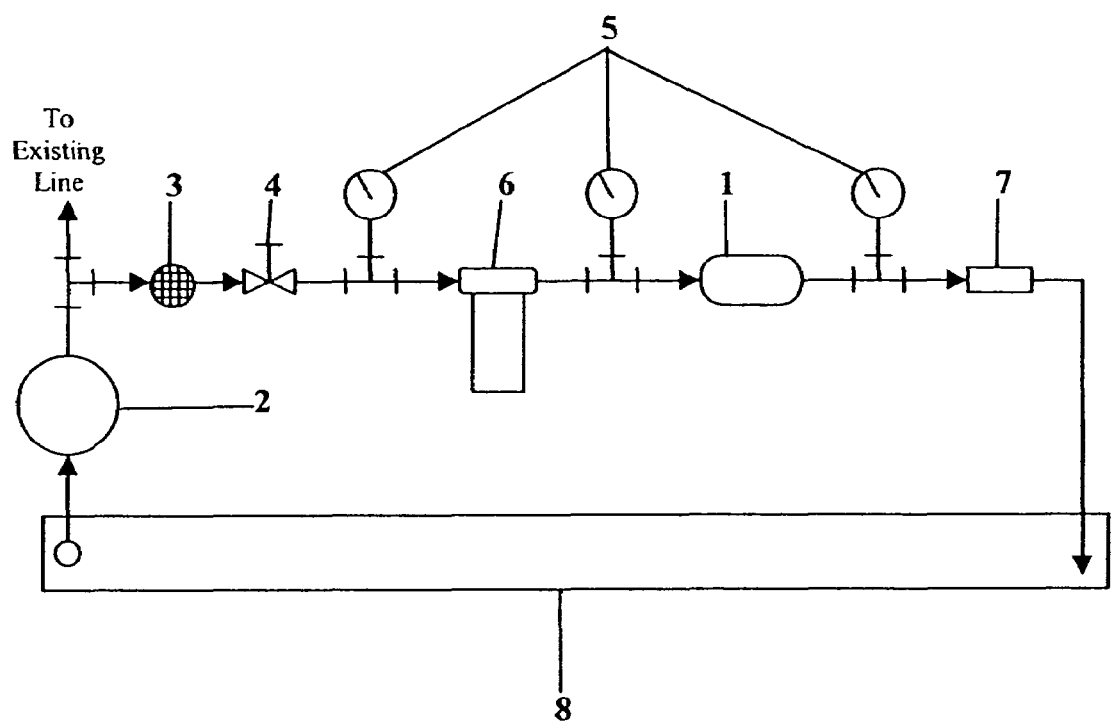
FIG. 1 is a schematic illustration of an inline configuration of the biocidal filter of the present invention.

The present invention provides a filter system, which is a simple and effective means to control microorganisms, such as bacteria, fungi, yeasts and the like, and slime in industrial process fluids, in particular, metalworking fluids such as recirculating cooling water systems that are used in conjunction with industrial fluid coolants such as straight oils, soluble oils, semi-synthetic type and synthetic type of coolants. The filter of the present invention works particularly well on soluble oils, semi-synthetic type and synthetic type of coolants. The filter of the present invention is easy to install, operate and replace. The filter is not affected by pH values, dissolved mineral levels, or temperatures commonly found in recirculating cooling water systems. The control of unwanted microorganisms and associated odors is achieved by passing the fluid in the recirculating cooling water system through the filter, which contains an iodinated resin. The iodinated resin inhibits the growth of microorganisms in the fluid, which is then cycled back into the system.

It has been found that the use of a biocidal filter containing an jodinate resin efficiently and conveniently extends the life of metalworking fluids that heretofore would have been discarded. The iodinated resin used in the filter is preferably a demand disinfectant, wherein iodine is released almost entirely on a demand-action basis. An example of a suitable iodinated resin usable for a filter of the present invention is described in (1) U.S. Pat. No. 5,639,452 which issued to Pierre Jean Messier on Jun. 17, 1997 and is entitled "Iodine/ Resin Disinfectant And A Procedure For The Preparation Thereof", incorporated herein by reference; and (2) patents cited therein as prior art, including U.S. Pat. Nos. 3,817,860, 3,923,665, 4,238,477 and 4,420,590. All of the above mentioned patents are incorporated herein by reference.

After a period of operation of the cooling system, for example, after a few days to a few weeks of operation, the used coolant is passed through a filter of the present invention. After filtration, the coolant does not contain detectable bacteria anymore and may be re-used. An advantage of this approach is that the biocide is not mixed in with the coolant and therefore does not render the coolant more toxic. When the iodinated resin of U.S. Pat. No. 5,639,452 is used, virtually no iodine bleeds into the coolant and also minimizes the toxicity and corrosiveness of the coolant.

The placement of the filter may be between the container containing the coolant solution that needs to be disinfected and a clean container that will accommodate the filtered solution. It is also possible to place a biocidal filter in the existing plumbing path of the machine's cooling system, or to create an alternative plumbing path for the circulating cooling system and place a biocidal filter in the alternative path.

The duration of the use of the filter will depend on the size of the cooling system. Preferably, the duration of the use should allow for the same number of gallons in the holding tank of the system to pass though the filter during each use. The operation can be repeated as necessary depending on the severity of contamination. For example, the filtering is run once every 3 to 30 days, preferably once every 7 to 14 days, i.e. 2-4 times a month. The filter should be replaced after filtering a certain amount of fluids. Preferably, for example, the filter should be replaced after filtering 1500 gallons for systems using synthetic and soluble oil coolants, 750 gallons for systems using semi-synthetic coolants, or as needed to provide satisfactory disinfection. A rinse solution is passed through the filter after use, preferably at the completion of each filtering cycle to rinse the filter, leaving the filter filled with the rinse solution between uses. The rinse solution may be water, an alcohol, C1-C6 carbon groups with at least one alcohol functional group in particular, such as methanol and ethanol, or a combination thereof. Preferably, the rinse solution is water or ethanol.

The following sections describe exemplary embodiments of the present invention. It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute terms, such as, for example, "should", "should not", "will," "will not," "shall," "shall not," "must," and "must not," are not meant to limit the scope of the present invention as the embodiments disclosed herein are merely exemplary.

An embodiment of the present invention with anticipated commercial potential will be referred to as Triosyn® T50-I Filter, which contains about 250 g of T50 iodinated resin beads made by Triosyn Research Inc., a division of Triosyn Corporation of Vermont, USA. All rights in Triosyn® T50-I Filter are expressly reserved.

To install the Triosyn® T50-I Filter, two different configurations are preferred. In both, the fluid leaves the tank, passes through the pump, prefilter, Triosyn T50-I Filter, flow control device, and returns to the tank. The first configuration, inline, uses the original equipment manufacturer's (OEM) machine pump to circulate fluid through the filter. The filter is installed as an alternative plumbing path of the central fluid circulation system. The second configuration, stand alone, uses its own pump, creating an independent system not connected to the existing plumbing. Both configurations employ the same flow control device to ensure the proper rate of flow through the filter, for example, to ensure that about 6 psi of pressure is supplied to the flow control device.

To install the Triosyn T50-I Filter in the inline configuration, the recirculating cooling water system and pump need to be turned off prior to installation. Referring to FIG. 1, the Triosyn T50-I Filter 1 is installed on the pressure side of the original equipment manufacturer's (OEM) machine pump 2. The plumbing is cut into and a tee fitting is inserted. Then the pre-existing line is re-connected. The plumbing is installed to lead to the screen. A screen 3, preferably a 40 mesh screen, is installed inline to trap large particulates, and it should be left accessible as it may be necessary to clear it occasionally. The system is plumbed according to FIG. 1 while the flow direction requirement of all components, including a needle valve 4, three pressure gauges 5 and a prefilter 6, is observed. Connect a return line to the flow control device 7 and place the open end in the cooling water tank 8. The needle valve 4 is used for adjusting the pump supply pressure. The pressure gauges 5 are preferably set at about 0-30 psi. The flow control device may be, for example, an orifice type of size 63. The prefilter 6 may be, for example, string wound polyethylene of 5 micron or better in diameter with a housing. Assorted plumbing fittings and flexible tubing may be ¼" NPT for system plumbing.

Figure 2:
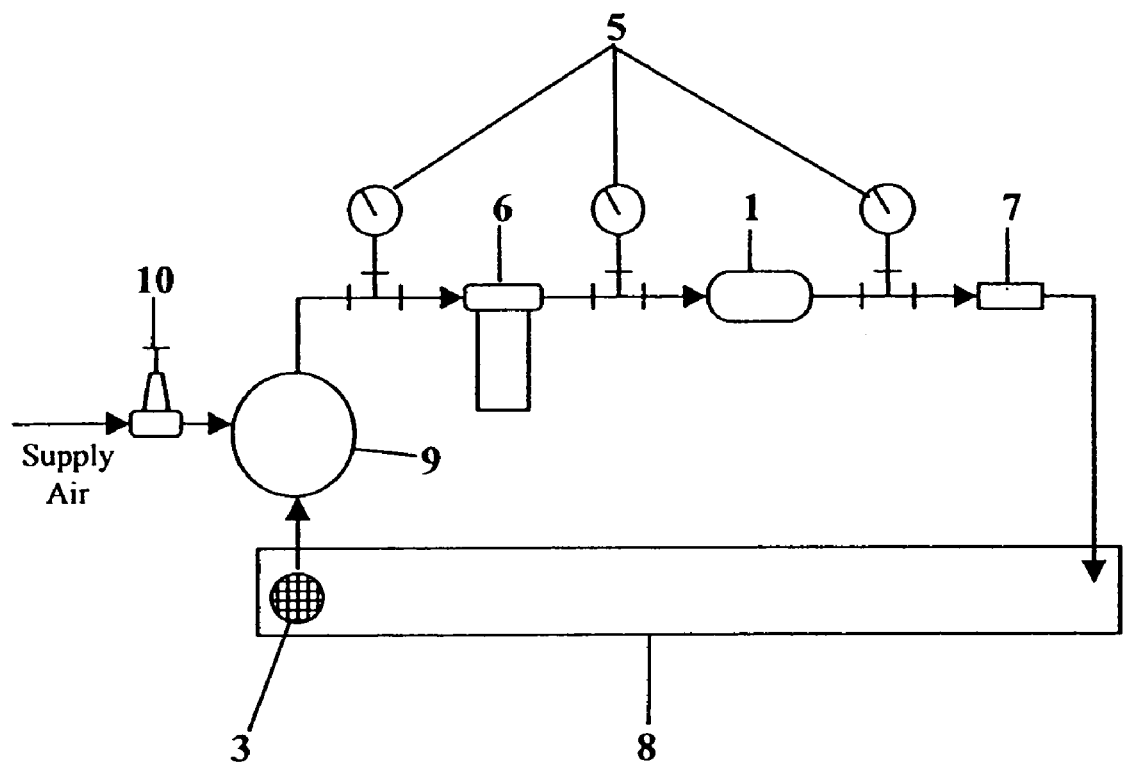
FIG. 2 is a schematic illustration of a stand alone configuration of the biocidal filter of the present invention.

To install the Triosyn T50-I Filter in the stand alone configuration, all of the components, including a pump 9, a pressure regulator 10, three pressure gauges 5, a prefilter 6, Triosyn T50-I Filter 1 and a flow control device 7, are assembled as shown in FIG. 2, while the flow direction requirement of all components is observed. The pump should not be connected to a power source or compressed air during assembly. The components may be installed on a cart or stand to facilitate use. The pump 9 may be an air driven diaphragm set at for example, ¼ gal/min at 50 psi min. The pressure regulator 10 is used for adjusting the pump air supply pressure.

During operation, the inlet and return lines are placed in the tank 8. The flow of the fluid to the filter in the inline configuration is commenced by opening the needle valve 4. In the stand alone configuration, the pump 9 is started to start to the flow to the filter. The needle valve 4 or pressure regulator 10 is adjusted to achieve a reading of an appropriate pressure, for example 6 psi on the flow control device pressure gauges 5, and the pressure is monitored during the operation. When properly installed and adjusted, the flow rate of the fluids through the Triosyn T50-I Filter 1 is about 1 gal/4 min. When finished, the inline needle valve 4 is closed or the stand alone pump 9 is stopped. For optimal performance, a large amount of water, for example 5 gallons of water, should be passed through the filter at the completion of each filtering cycle to rinse the filter, leaving the filter filled with water between uses. Other suitable solutions such as an alcohol, preferably ethanol, may also be used to rinse the filter.

For replacement of the Triosyn T50-I Filter 1, it should be replaced when no flow is running through the system. The Triosyn T50-I Filter 1 is removed from the system and replaced with a new T50-I Filter. Then all lines are reattached, and the new filter is ready for use.

The prefilter 6 may also require occasional replacement. The pressure gauges 5 before and after the prefilter 6 may be used as a guide for its replacement.

If large metal chips are taken up in the inline system, it may be necessary to clear the screen 3 occasionally. With the pump off, the attachments are removed and the screen 3 is cleared and then replaced.

EXAMPLES OF COOLANT ADDITIVES

1. Semi-Synthetic #1

Sodium Sulfonate: Acts as an emulsifier

Naphtenic Base Stock (Refined): Oil used for lubrication 1,2,3-Propanetriol (Glycerine): It is produced by the hydrolysis of fats, dissolves easily in the coolant because of its alcohol functional groups. It is used in the coolant for lubrication.

1,2-Propanediol (Glycols): Used in cars as anti-freeze. In the coolant, it may be used for coating/lubrication of the machines.

Triethanolamine: Acts as a surfactant (anionic or nonionic)

Amine Carboxylate (Monoethanolamine): Used as a corrosion inhibitor and also as a surfactant.

Amine Triazine: Acts as a biocide

Sodium Pyrithione: Acts as an anti-fungal and anti-bacterial agent

Tetrasodium EDTA Salts: Salt that easily dissolves in the coolant and that acts as a chelating agent for metals present in the solution. It may also act as a stabilizing agent.

Silicone Based Antifoam: Helps reduce foaming of the coolant

2. Semi-Synthetic #2

Sodium Sulfonate: Acts as an emulsifier

Paraffinic Base Stock (Refined): Oil used for lubrication

Triethanolamine: Acts as a surfactant (anionic or nonionic)

Amine Carboxylate (Monoethanolamine): Used as a corrosion inhibitor and also as a surfactant Amine Triazine: Acts as a biocide Sodium Pyrithione: Acts as an anti-fungal and anti-bacterial agent Tetrasodium EDTA Salts: Salt that easily dissolves in the coolant and that acts as a chelating agent for metals present in the solution. It may also act as a stabilizing agent.

Silicone Based Antifoam: Helps reduce foaming of the coolant

3. Synthetic
  Triethanolamine: Acts as a surfactant (anionic or nonionic)
  Isobutanol-2-amine: Acts as a surfactant
  Polyalkylene Glycol: Used in cars as anti-freeze. In the coolant, it may be used for coating/lubrication of the machines.
  Polyoxyl methyl-1-2-ethandiyl: Used for lubrication
  Sodium Pyrithione: Acts as an anti-fungal and anti-bacterial agent
  Silicone base antifoam: Helps reduce foaming of the coolant 4. Soluble Oil Soluble oil is a combination of 30-85% of severely refined mineral oil and emulsifiers to help disperse the oil in water. The fluid concentrate usually includes other additives to improve performance and lengthen the life of the fluid. Soluble oil products are supplied as concentrates that are diluted with water to obtain the working fluid. Depending on the fluid and the application, the concentrate may be diluted one part concentrate to five parts of water up to one part concentrate to forty parts of water (17% to 2.4%).

Having now described one or more exemplary embodiments of the invention, it should be apparent to those skilled in the art that the foregoing is illustrative only and not limiting, having been presented by way of example only. All the features disclosed in this specification (including any accompanying claims, abstract, and drawings) may be replaced by alternative features serving the same purpose, and equivalents of similar purpose, unless expressly stated otherwise. Therefore, numerous other embodiments of the additions and modifications thereof are contemplated as falling within the scope of the present invention as defined by the appended claims and equivalents thereto.

The invention claimed is:

1. A method of controlling the growth of microorganisms in a metalworking fluid, comprising passing said metalworking fluid through a filter containing a demand disinfectant, said demand disinfectant being an iodinated resin and iodine is released almost entirely on a demand-action basis, wherein said resin inhibits the growth of the microorganisms, and virtually no iodine bleeds into the metalworking fluid.

2. The method of claim 1, wherein said iodinated resin comprises an iodinated anion exchange resin.

3. The method of claim 1, wherein said iodinated resin comprises an iodinated strong base anion exchange resin.

4. The method of claim 1, wherein said metalworking fluid is selected from the group consisting of soluble oil, semi-synthetic, synthetic type of coolants and combinations thereof.

5. The method of claim 1, wherein said metalworking fluid is a semi-synthetic or synthetic type of coolant.

6. The method of claim 1, wherein said metalworking fluid is a recirculating coolant of a recirculating cooling system.

7. The method of claim 6, wherein said filter is located in a flow path of said recirculating coolant.

8. The method of claim 7, wherein said fluid recirculates through said filter.

9. The method of claim 6, wherein said filter is located in a recirculating path of said recirculating coolant.

10. The method of claim 6, wherein said filter is located in an alternative flow path of said recirculating coolant, said alternative flow path is created for placing said filter and passing said coolant through said filter.

11. The method of claim 1, wherein said fluid passes through said filter once every 3-30 days.

12. The method of claim 11, wherein said fluid passes through said filter once every 7-14 days.

13. The method of claim 1, wherein said filter is rinsed with a rinse solution after use.

14. The method of claim 13, wherein said rinse solution is water, an alcohol or a mixture thereof.

15. The method of claim 14, wherein said alcohol is a C1-C6 carbon group having at least one alcohol functional group.

16. The method of claim 14, wherein said rinse solution is water.

17. The method of claim 14, wherein said rinse solution is ethanol.

18. The method of claim 1, further comprising passing a rinse solution through said filter at the completion of each filtering cycle to rinse said filter.

19. The method of claim 18, further comprising leaving the filter filled with said rinse solution between filtering cycles.

20. The method of claim 18, wherein said rinse solution is water, an alcohol or a mixture thereof.

21. The method of claim 20, wherein said alcohol is a C1-C6 carbon group having at least one alcohol functional group.

22. The method of claim 20, wherein said rinse solution is water or ethanol.

* * * * *